United States Patent [19]

Owen

[11] Patent Number: 5,742,234
[45] Date of Patent: Apr. 21, 1998

[54] PARTICLE DETECTION AND DESTRUCTION IN FLUID SYSTEMS

[75] Inventor: Allan B. Owen, Exton, Pa.

[73] Assignee: Vickers, Inc., Maumee, Ohio

[21] Appl. No.: 395,845

[22] Filed: Feb. 28, 1995

[51] Int. Cl.⁶ ..................................... G08B 17/00
[52] U.S. Cl. .......... 340/631; 340/620; 340/627; 200/61.09; 73/10; 324/204; 324/219; 324/511
[58] Field of Search .................. 340/627, 631, 340/620; 73/10; 324/204, 219, 511; 200/61.09

[56] References Cited

U.S. PATENT DOCUMENTS

| | | | |
|---|---|---|---|
| 3,193,815 | 7/1965 | Prestel | 340/631 |
| 3,622,822 | 11/1971 | Gardner | 310/89 |
| 4,070,660 | 1/1978 | Tauber | 340/631 |
| 4,127,808 | 11/1978 | Sproul | 340/698 |
| 4,219,805 | 8/1980 | Magee et al. | 340/631 |
| 4,302,754 | 11/1981 | Magee et al. | 340/631 |
| 4,598,280 | 7/1986 | Bradford | 340/631 |
| 5,250,909 | 10/1993 | Bitts | 324/542 |

Primary Examiner—Jeffery Hofsass
Assistant Examiner—Julie B. Lieu
Attorney, Agent, or Firm—Barnes, Kisselle, Raisch, Choate, Whittemore & Hulbert

[57] ABSTRACT

Apparatus for monitoring particles in fluid systems in which a detector has electrical contacts that are bridged by particles captured from suspension in the fluid. Upon detection of a particle, a control microprocessor stores a predetermined quantity of electrical energy on a capacitor, which is then discharged through an inductor to burn off the particle at the detector. The burn-off charge and return lines from the charge storage capacitor are un-grounded, and are connected by respective electronic switches through relay contacts to the conductors connected to the chip detector. The relay contacts are also connected to the inputs of a differential amplifier for detecting presence of a chip bridging the detector contacts and monitoring continuity of the conductors to and from the detector. The relay is powered by system voltage, and in the event of system power failure connects the chip detectors directly to warning lamps on an operator panel.

52 Claims, 8 Drawing Sheets

PARTICLE DETECTION AND DESTRUCTION IN FLUID SYSTEMS

The present invention is directed to a device, commonly referred to as a "chip detector," for detecting suspension of particulate debris in fluid systems. More specifically, the invention is directed to a device and method for both detecting such particles and destroying such particles, commonly referred to as "fuzz burning," when the particles are of relatively small size.

BACKGROUND AND OBJECTS OF THE INVENTION

Conventional debris monitoring and detection systems include one or more chip detectors connected by cables to monitoring and detecting circuitry. The detectors have electrical contacts disposed in fluid, and a magnet for attracting ferromagnetic particles suspended in the fluid into a position bridging the contacts of the detector. When the particle bridges the detector contacts, current through the interconnection cable illuminates a warning lamp. Particle detection systems of the described character are particularly useful in monitoring aircraft lubrication oil systems, with the detector (s) being disposed at the lubricated component(s) and the warning lamp disposed at a pilot or maintenance panel. Presence of a chip at the detector may indicate deterioration of the system components, and may call for immediate landing and maintenance on the aircraft.

U.S. Pat. No. 4,070,660, assigned to the assignee hereof, discloses a particle detection system of the described character that includes the additional capability of removing small particles from the detector during normal operation by discharging energy stored on a capacitor across the detector contacts. If the particle or "fuzz" is of sufficiently small size, the electrical energy discharged across the detector contacts will effectively burn off the particle. A modification disclosed in the noted patent contemplates provision of capacitors of differing size and energy storage capability, and an operator switch for selectively connecting the chip detector to the capacitors in turn. In this way, the operator can obtain information about the size of the particles being detected by correlation with the quantity of energy needed to burn off the particles. If the detected particle is of a size that cannot be burned off, immediate landing and maintenance may be required.

Although particle detection systems of the described character have enjoyed substantial commercial acceptance and success, further improvements remain desirable. For example, it has been proposed to make the burn-off operation automatic upon detection of a particle or chip at the detector gap. However, systems that embody such automatic burn-off capability have been of static or rigid design, and not readily adaptable or programmable in the field, either during system set-up or during actual operation. Another problem encountered with conventional chip detection and burn-off systems lies in the high electrical stress placed on the system components, and emission of electromagnetic interference, due to the rapid discharge of the stored burn-off energy at high current over a very short time duration. Radiation of electromagnetic interference can be particularly deleterious in aircraft applications.

It is therefore a general object of the present invention to provide an apparatus and method for monitoring particles in fluid systems that overcome one or more of the disadvantages in prior art systems discussed above. Another and more specific object of the present invention is to provide particle detection apparatus of the described character that is of compact size, and thus can be readily employed in aircraft applications where available space is at a premium, and which operates at reduced power consumption as compared with similar devices previously proposed.

Another object of the present invention is to provide a particle detection apparatus and method of the described character that can be employed in conjunction with one or a plurality of chip detectors, and which can be readily programmed in the field during set-up or normal operation for applying differing burn-off energies to different detectors. Another object of the present invention is to provide a particle detection apparatus and method of the described character that exhibit reduced electrical stress on system components and reduced emission of electromagnetic interference during a particle burn-off operation. A further object of the present invention is to provide a particle detection system of the described character that has a fail-safe mode of operation in which the particle detectors are connected directly to particle indicators at the pilot or maintenance panel in the event of power loss at the system electronics. Yet another object of the present invention is to provide an apparatus and method of the subject character that can be employed in conjunction with either grounded or un-grounded particle detectors.

SUMMARY OF THE INVENTION

Apparatus for monitoring particles in fluid systems in accordance with the present invention includes at least one detector for positioning in a fluid system and having electrical contacts to be bridged by particles suspended in system fluid. An electronic control system includes circuitry coupled to the detector for detecting presence of a particle bridging the detector contacts, and one or more capacitors for storing electrical energy to burn off particles at the detector. In accordance with a first important feature of the present invention, the control circuitry includes facility for charging the storage capacitor(s) to a predetermined level associated with the detector at which the particle has been detected, and then discharging the capacitor(s) into the detector across the detector contacts to burn off particles bridging the detector contacts. The control circuitry monitors the level of energy stored on the energy storage capacitor(s) during a charging mode of operation, and terminates the charging mode of operation when the desired preselected energy level has been reached. In this way, burn-off energy can be preselected or preprogrammed for each detector channel independently, and thereby accommodate differing detector operating characteristics, differing interconnection cable lengths, etc.

In the preferred embodiment of the invention, the charge stored on the burn-off capacitor(s) is incremented or pumped during the charging mode of operation by a d.c.-to-d.c. convertor. This converter includes an inductance and an electronic switch that is responsive to a pulsed control signal from a control microprocessor for drawing current through the inductance and thereby storing electromagnetic energy in the inductance during half cycles of one polarity of the control pulse sequence, and then discharging the energy stored in the inductance into the charge storage capacitor(s) during half-cycles of the pulsed control signal of opposing polarity. The incremental increase in stored energy is continuously monitored, and terminated when the stored energy reaches the desired level. In this way, burn-off energy is closely controlled for each detector channel.

In accordance with another feature of the present invention, which can be employed separately from or in combination with other features of the invention, the charge storage capacitor or capacitors are connected to discharge into the chip detector through an inductor. This inductor controls the shape of the discharge current pulse by increasing the duration of pulsed discharge and reducing discharge peak amplitude, while not affecting total discharge energy. In this way, electrical stress on the switches that apply the discharge energy to the chip detectors is greatly reduced, and emission of electromagnetic radiation is reduced or eliminated. This feature of providing an inductor in the burn-off energy discharge path can be readily implemented by retrofit in existing particle detection systems.

A further feature of the present invention, which again can be employed either in combination with or separately from other features of the invention, lies in the fact that all connections to and from the chip detector(s) are by means of un-grounded differential connections. That is, the burn-off energy storage capacitor bank has discharge and return lines that are connected through respective electronic switches to conductors connected to the respective chip detector contacts. A differential amplifier has inputs connected to such conductors for detecting presence of a particles across the detector contacts. The differential amplifier is also employed for monitoring continuity of the conductors connected to the chip detector as a function of current flowing through the conductors to and from the chip detector. An electronic switch at each chip detector channel is responsive to a control signal from the control microprocessor for altering the input impedance characteristics of the differential amplifier for particle detection and continuity monitoring modes of operation. In this way, the detection and burn-off circuitry of the present invention can be employed in conjunction with either grounded or un-grounded chip detectors.

In accordance with yet another feature of the invention, which can be employed alone or in combination with other features, relays have contacts that alternately connect the chip detector conductors to the differential output of the burn-off capacitor bank and the inputs of the differential amplifier, or directly to chip detection indicators. The relays are powered by system power so that, in the event of system power failure, the chip detectors are connected directly to lamps or other indicators at the pilot or maintenance panel, and thus can function as in the prior art in the event of system failure. The control microprocessor in the preferred embodiment of the invention has a digital input/output port through which connection can be made to the control electronics for maintenance or set-up purposes. The control electronics may include non-volatile memory for storing programming and event information obtained during operation, which can be downloaded for analysis through the input/output port. The various functions of the control electronics may be energized by an operator through the input/output port for maintenance purposes independent of chip detection at the detectors.

BRIEF DESCRIPTION OF THE DRAWINGS

The invention, together with additional objects, features and advantages thereof, will be best understood by the following description, the appended claims and accompanying drawings in which:

DETAILED DESCRIPTION OF PREFERRED EMBODIMENTS

Figure 1:
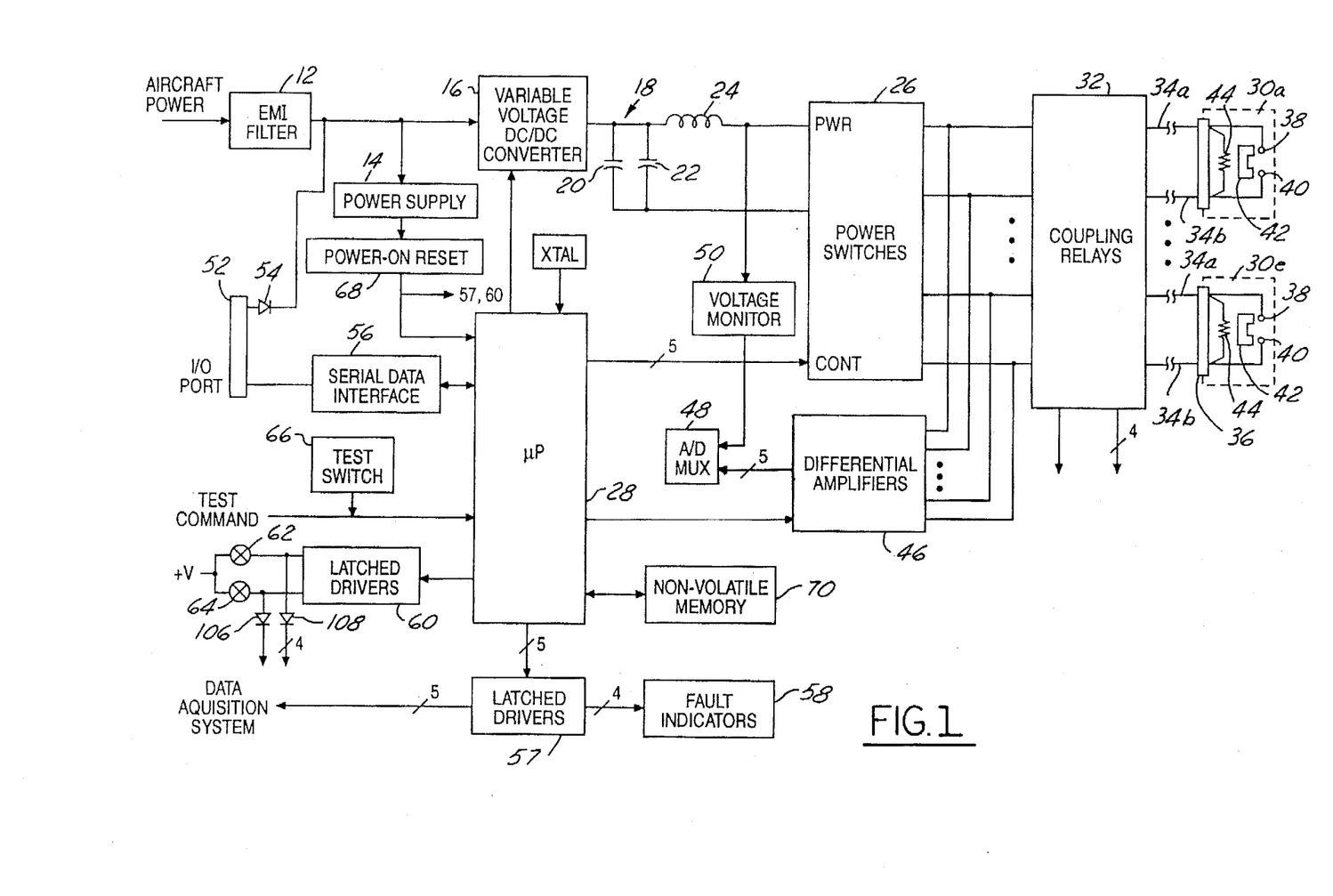
FIG. 1 is a functional block diagram of a chip detection and burn-off system in accordance with one embodiment of the present invention.

FIG. 1 illustrates an apparatus 10 for monitoring particles in an aircraft lubrication oil system in accordance with a presently preferred embodiment of the invention. Aircraft electrical power, typically at twenty-eight volts d.c., is fed through an EMI filter 12 to a power supply 14, and to a variable voltage d.c./d.c. convertor 16. Power supply 14 supplies electrical power to the remainder of the system circuitry. The output of variable voltage d.c./d.c. convertor is connected to a capacitor bank 18 comprising a pair of parallel charge storage capacitors 20,22. The discharge side of capacitors 20,22 is connected through an inductor 24 to the power input of a bank of power switches 26, and the return side of capacitors 20,22 is connected directly to power switches 26. Power switches 26 also receive switch control inputs from a control microprocessor 28.

Power switches 26 have a number of parallel differential output channels corresponding to the number of chip detectors in the debris monitoring system. In the particular example illustrated in the drawings for helicopter lubricant debris monitoring applications, there are five chip detectors 30a–30e (FIGS. 1 and 3C) that are to be monitored and controlled. The output of each power switch 26a–26e (FIG. 2C) comprises a pair of differential output lines connected to the corresponding channel of a series of coupling relays 32. Each relay channel is connected by a twisted pair of conductors 34a,34b to a remote chip detector connector 36. Each chip detector 30a–30e comprises a permanent magnet 42 and a pair of electrical contacts 38,40 disposed within a fluid sump or stream such that particles are attracted by magnet 42 and bridge detector contacts 38,40. A resistor 44 is connected across the terminals of connector 36 for supplying a current path to monitor continuity of conductors 34a,34b, as will be described.

Each chip detector channel is connected between power switches 26 and coupling relays 32 to corresponding inputs of a set of differential amplifiers 46 for both detecting presence of a chip bridging contacts 38,40 of any of the chip detectors 30a–30e, and monitoring continuity of the chip detector conductors 34a,34b of each detector channel. The outputs of differential amplifiers 46 are connected to corresponding inputs of an a/d multiplexer 48, which receives another input from a voltage monitor 50 connected across capacitor bank 18. The output of a/d multiplexer 48 provides an input to microprocessor 28. Microprocessor 28 also has input/output ports connected through a serial data interface 56 to a serial data input/output port 52. Port 52 may also be connected through a diode 54 to the power bus input to power supply 14 for supplying power to the control circuitry independent of aircraft power for set-up or maintenance purposes. Microprocessor 28 also has five output lines connected to a bank of latched drivers 57, which provide outputs to on-board or remote fault indicators 58, as well as fault outputs for a remote data acquisition system. Microprocessor 28 also has an output port connected to a pair of latched lamp drivers 60, which drive a pair of indicator lamps 62,64. Microprocessor 28 has an input port that receives a test command either from a remote data acquisition system, or from an on-board test switch 66. Microprocessor 28, latched drivers 57 and latched lamp drivers 60 all receive reset inputs from a power-on reset circuit 68 for resetting the control circuitry when power is initially applied to apparatus 10. The internal clock of microprocessor 28 is converted to a crystal 71.

Microprocessor 28 is also connected to a non-volatile memory 70 for storing information indicative of chip detection events incurred during operation for later read-out at serial port 52, or for storing program or test information. For example, microprocessor 28 can be programmed to store chip detector and burn-off information in memory 70, the frequency of which can provide information indicative of a need for maintenance. Microprocessor 28 can also be programmed, in the event of an unsuccessful burn-off attempt, automatically to increase the burn-off energy at capacitor bank 18 and attempt another burn-off. Again, information indicative of the frequency and energy level of burn-off attempts can be stored in memory 70 for later analysis.

Figure 3A:
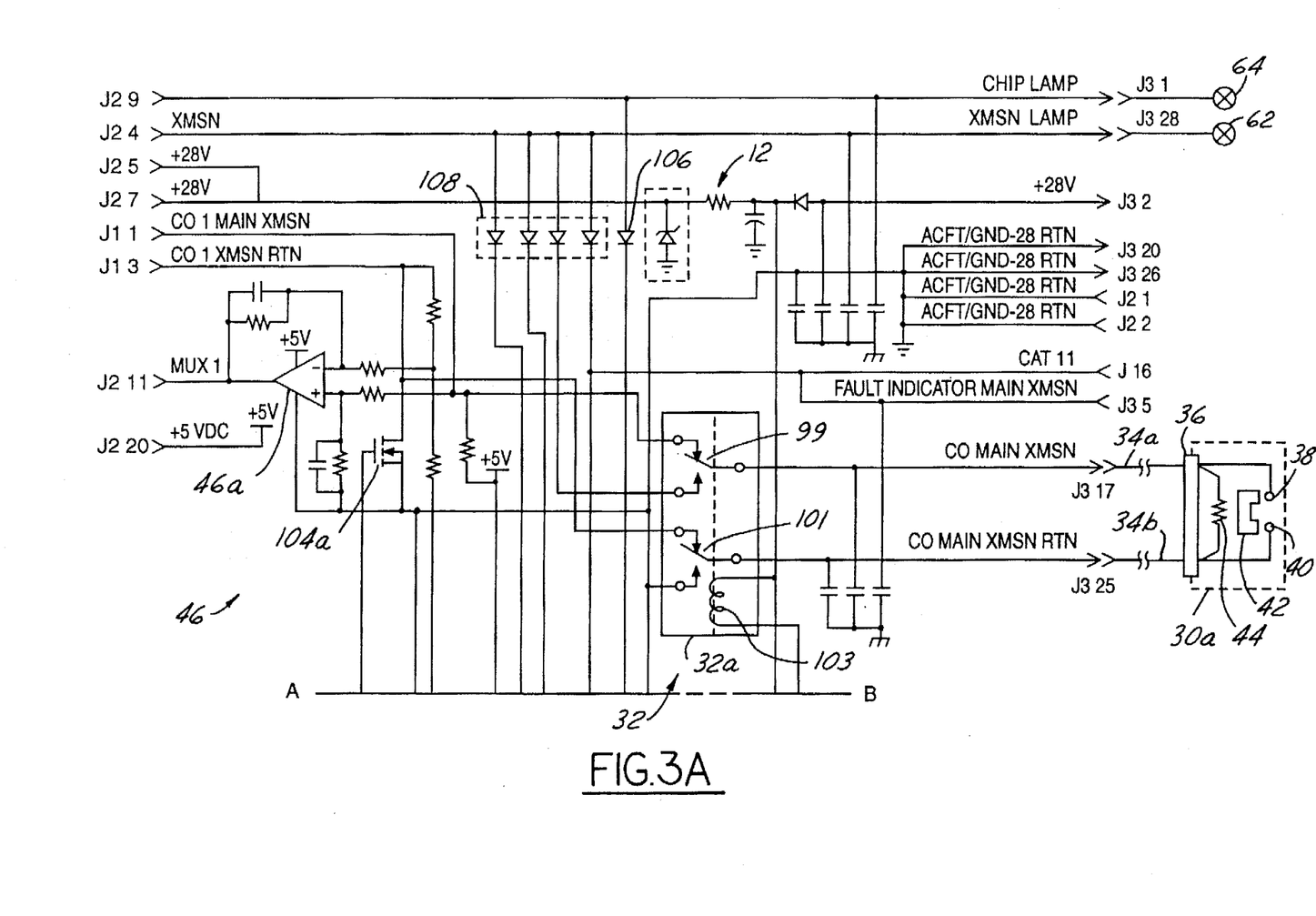
Figure 3B:
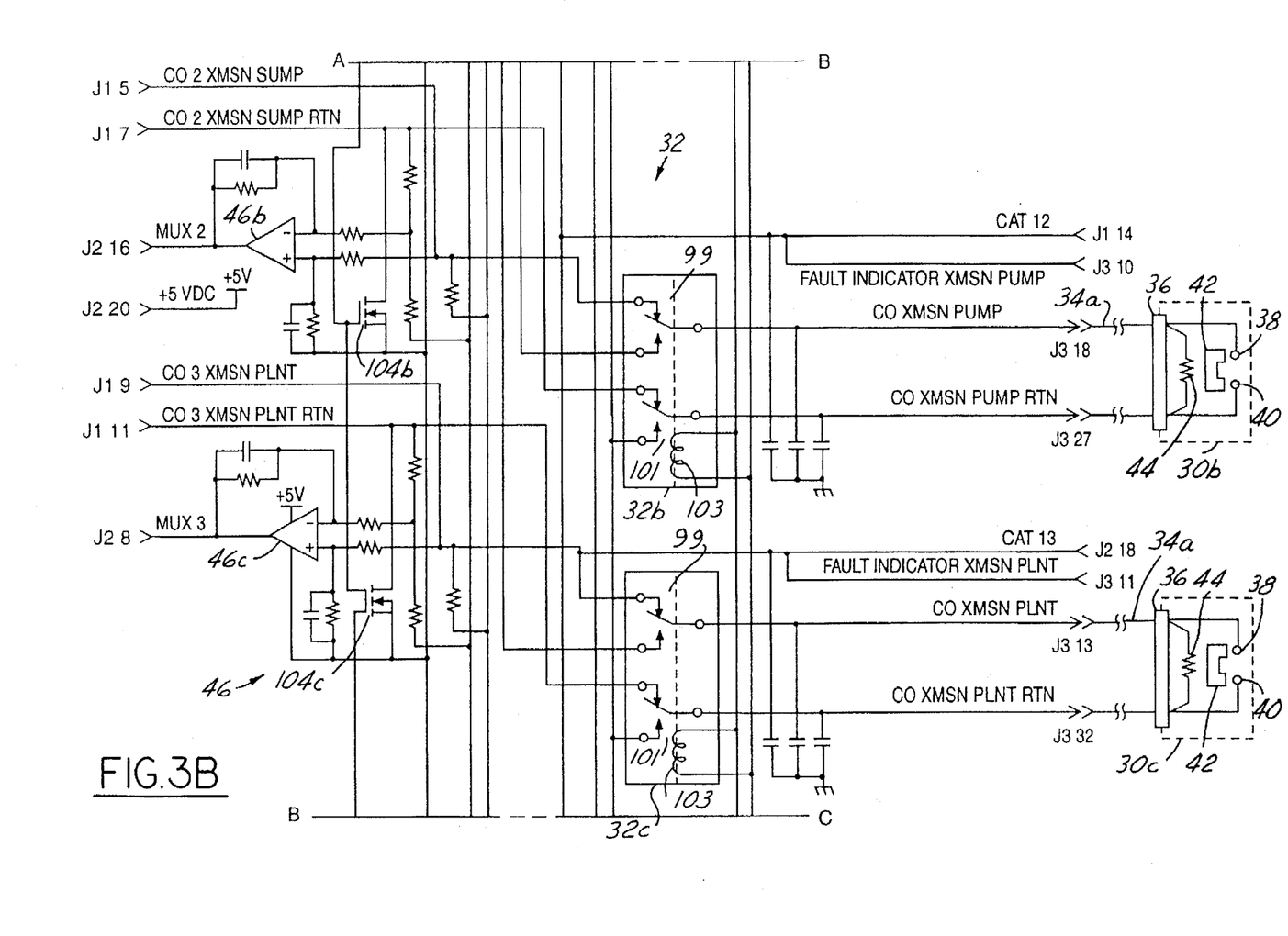
Figure 3C:
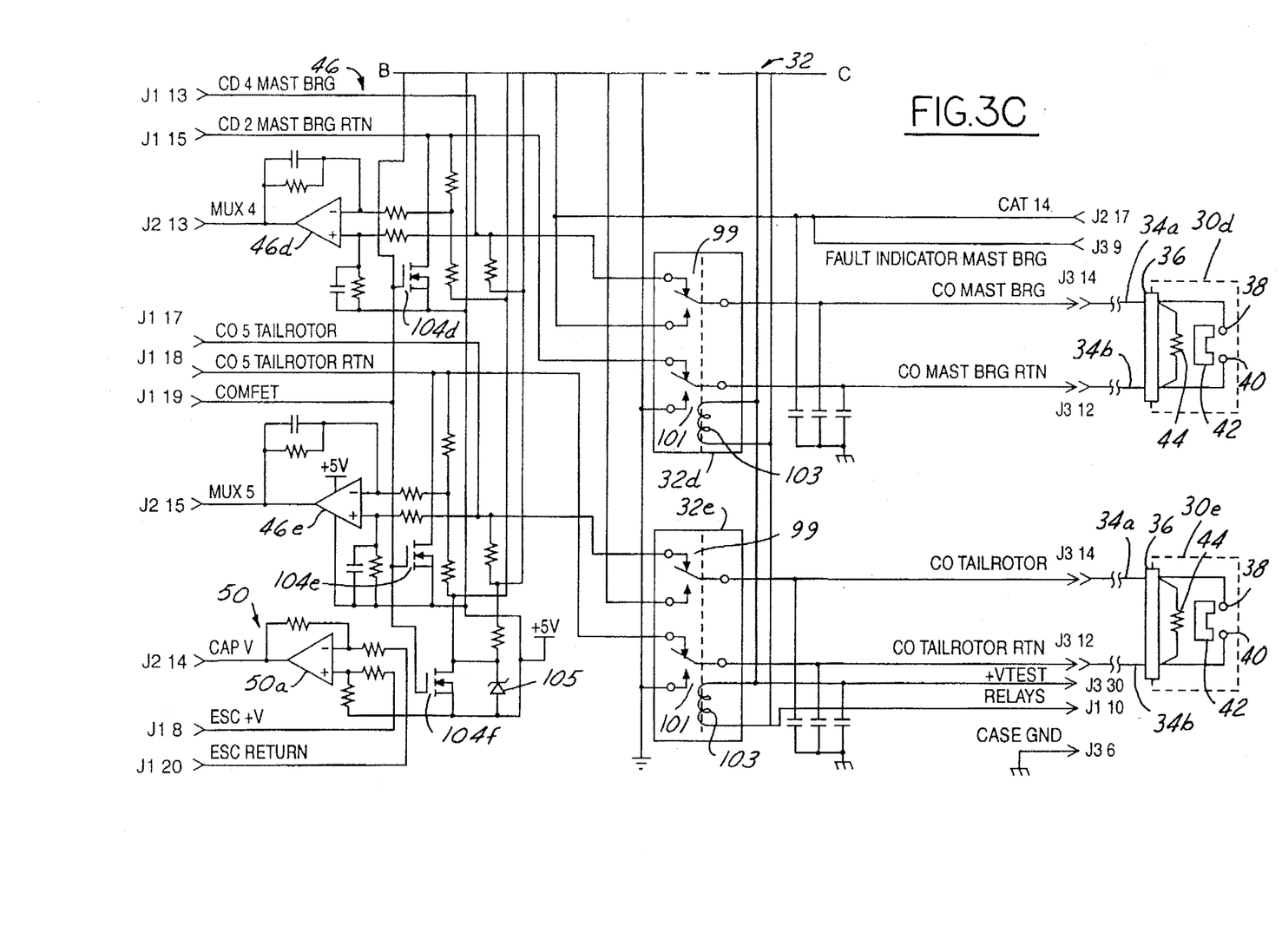

In general operation, each chip detector 30a–30e is monitored by a corresponding differential amplifier 46 (46a–46e in FIGS. 3A–3C). When a chip is detected across the contacts 38,40 of any chip detector, such as chip detector 38a, the resulting short-circuit condition at the detector is fed by differential amplifier 46a (FIG. 3A) through multiplexer 48 to microprocessor 28, which indicates a chip event. Upon detection of the chip event, variable voltage d.c./d.c. convertor 16 is energized by microprocessor 28 to charge capacitor bank 18. The charge across capacitor bank 18 is monitored by voltage monitor 50 and multiplexer 48. Each chip detector channel has a corresponding burn-off energy level stored in microprocessor 28 or non-volatile memory 70. These burn-off energy levels may vary among the chip detector channels due to a variety of conditions, such as cable length, chip detector type and condition, etc. When the charge across capacitor bank 18 reaches the desired level corresponding to the channel at which the chip has been detected, microprocessor 28 de-energizes convertor 16, and energizes the pair of power switches 26 associated with that chip detector channel. In this connection, it is to be noted that, since the energy stored on capacitor bank 18 is that desired for a specific chip detector channel, burn-off is to be attempted at only one channel at a time.

In any event, the energy stored on capacitor bank 18 is fed by power switches 26 (e.g., switch 26a in FIG. 2D) and coupling relays 32 (e.g., relay 32a in FIG. 3A) to the appropriate chip detector (e.g., chip detector 30a). If the chip that bridges contacts 38,40 is sufficiently small, this energy will burn off the chip particle. On the other hand, if the stored energy is insufficient to burn off the chip particle, presence of the chip across contacts 38,40 will continue to be detected by differential amplifiers 46 (e.g., amplifier 46a in FIG. 3A) and microprocessor 28. Microprocessor 28 then activates the appropriate latched driver 57 to indicate a fault condition at 58, and latches the appropriate lamp driver 60 to illuminate one of the lamps 62,64. Differential amplifiers 46 also monitor continuity of conductors 34a,34b in each chip detector channel as a function of current flowing through the associated resistor 44. In the event of current interruption, indicating failure at the chip detector or rupture of one of the conductors, microprocessor 28 latches the appropriate drivers 57,60 setting the appropriate fault indicator 58 and illuminating the appropriate lamp 62 or 64. A continuity check may also be initiated by test switch 66 or a test command from a remote data acquisition system.

Figure 2A:
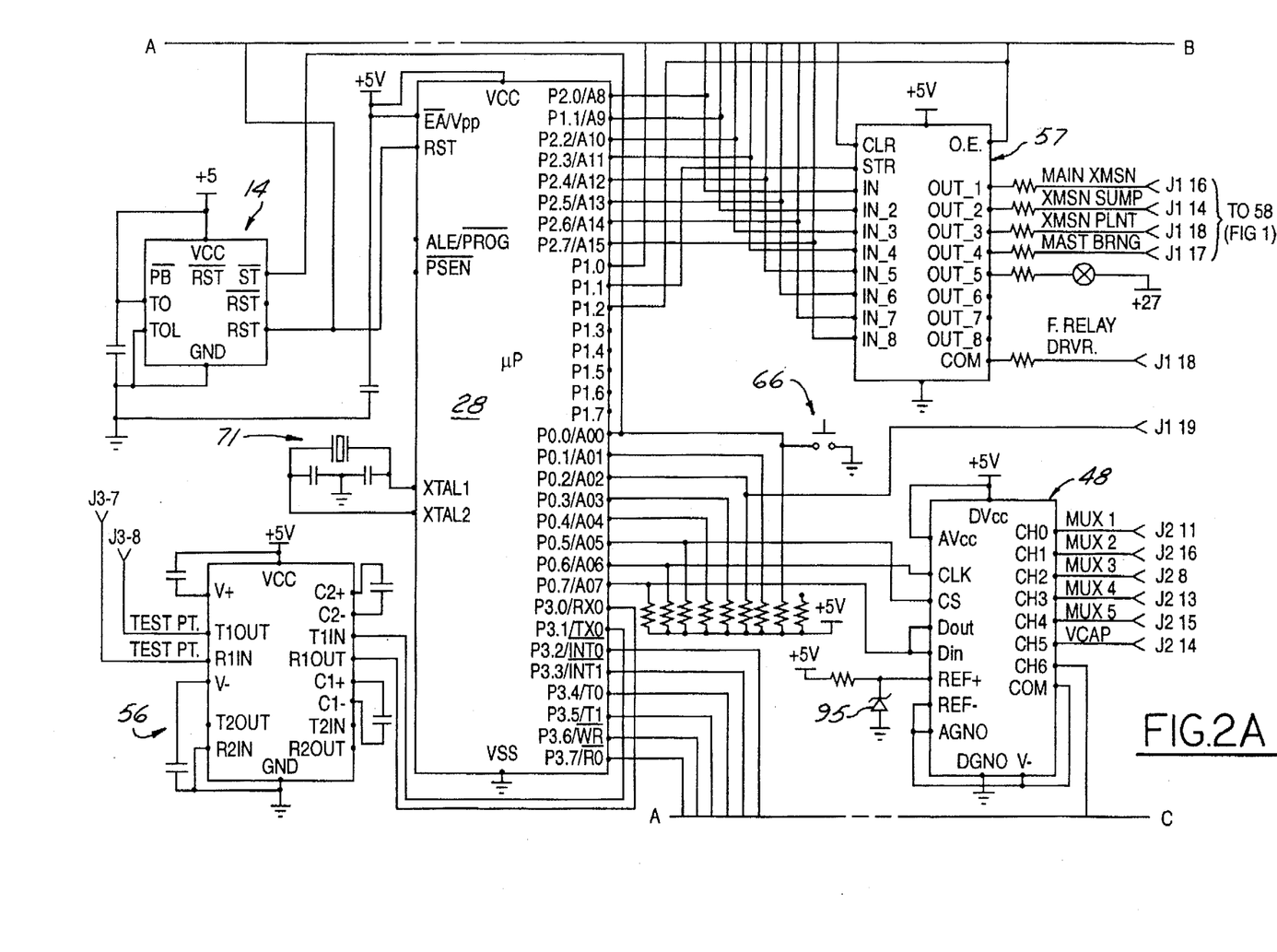
FIGS. 2A, 2B, 2C, 2D and 2E and FIGS. 3A, 3B, 3C together comprise an electrical schematic diagram of a presently preferred implementation of the system functionally illustrated in FIG. 1.
Figure 2B:
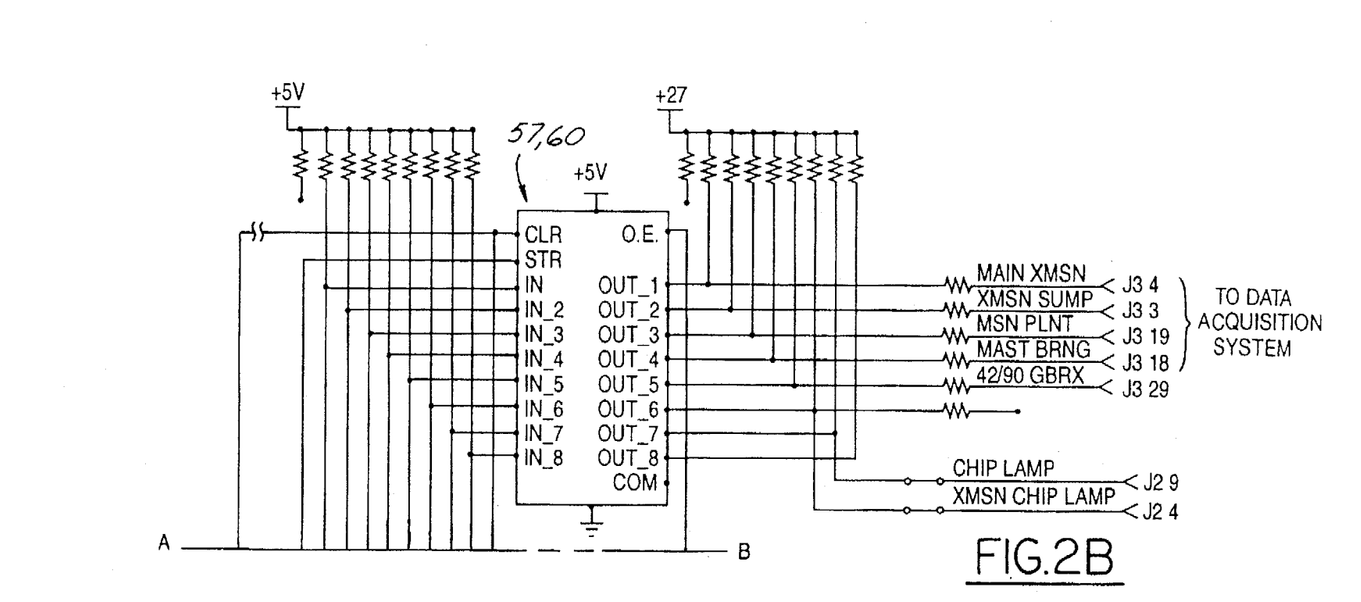
Figure 2C:
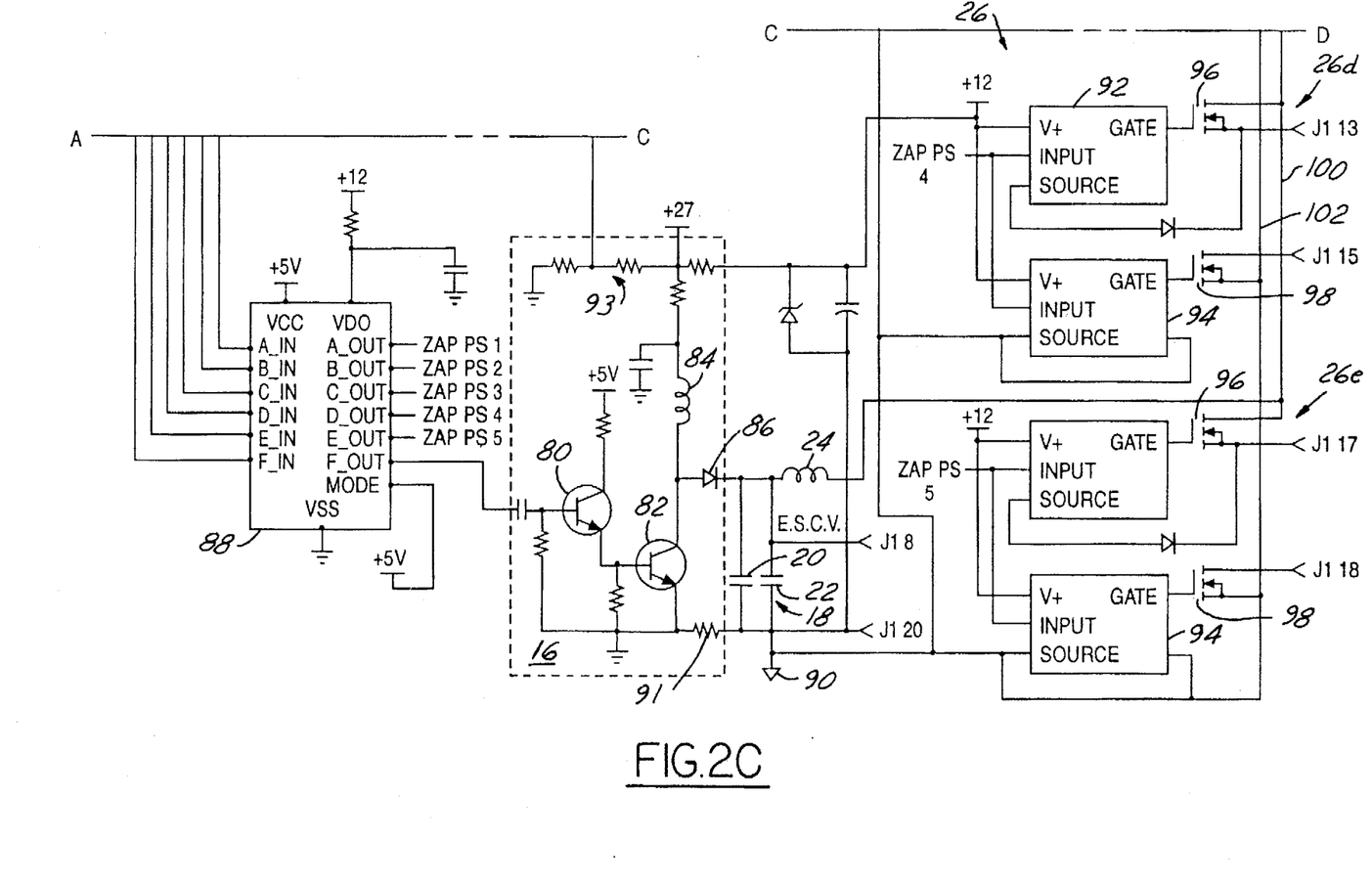
Figure 2D:
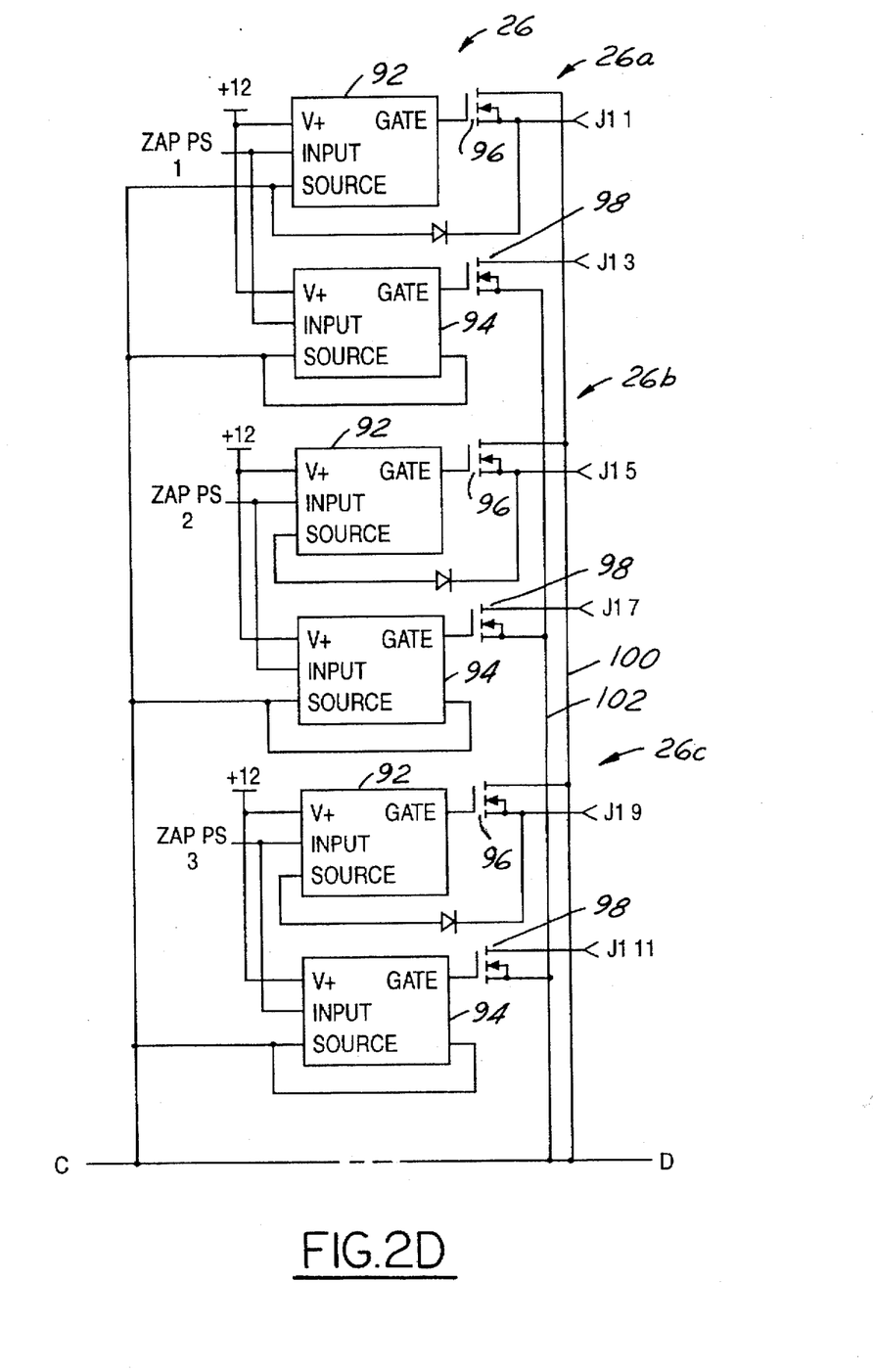
Figure 2E:
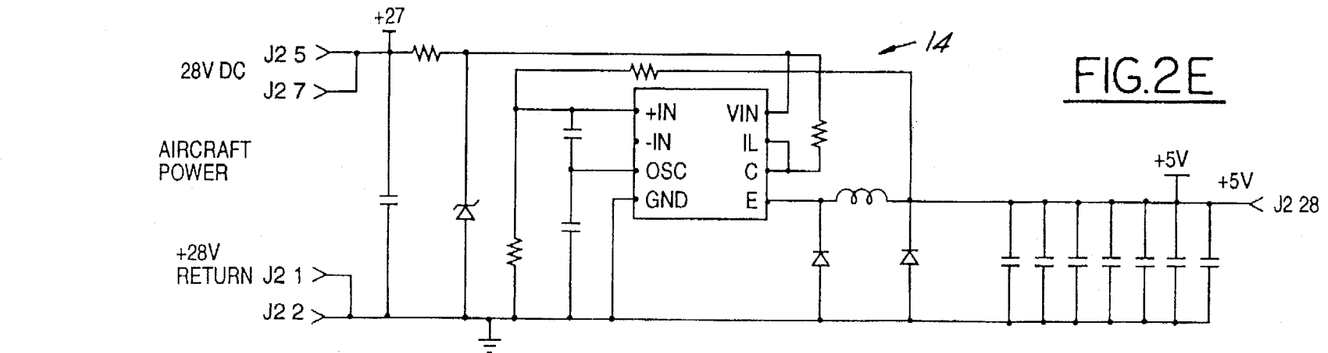

FIGS. 2A–2E and FIGS. 3A–3C are electrical schematic diagrams of respective circuitboards of a system implementing the subject matter disclosed in functional block form in FIG. 1, with the exception of non-volatile memory 70 (FIG. 1), the remote test command input and input/output port power feed 54, which are not implemented in the embodiment of FIGS. 2A–2E and 3A–3C. FIGS. 2A and 2B are interconnected along the line A–B in each figure, FIGS. 2A and 2C are interconnected along the line A–C in each figure, and FIGS. 2C and 2E are interconnected along the line C–E in each figure. FIGS. 3A and 3B are interconnected along the line A–B in each figure, and FIGS. 3B and 3C are interconnected along the line B–C in each figure. The circuitboard of FIGS. 2A–2E is interconnected with the circuitboard of FIGS. 3A–3C by the connectors J1 and J2 illustrated in each figure. Connector J3 provides connection to components external to the two circuitboards—e.g., chip detectors 32a–32e, serial input/output port 52, lamps 62,64, aircraft power and ground, and the remote data acquisition system. Reference numerals employed above in connection with FIG. 1 are also employed in FIGS. 2A–2E and 3A–3C to indicate corresponding identical elements or components groups.

Referring to FIGS. 1 and 2C, variable voltage d.c./d.c. convertor 16 includes a pair of transistors 80,82, the latter being connected in series with an inductance 84 across aircraft power. A diode 86 connects the junction of transistor 82 and inductance 84 to capacitor bank 18. Convertor 16 receives a pulsed control input from microprocessor 28 FIG. 1 and 2A) through channel F of a buffer 88 (FIG. 2C). The control signal supplied by microprocessor 28 to convertor 16, which only occurs after a chip has been detected at one of the chip detectors as described above, comprises a continuing pulsed digital signal consisting of alternating portions of opposite polarity (high and low). When the input to the base of transistor 80 is high, transistors 80,82 are conductive, and current is drawn through inductance 84 by transistor 82. This current in inductance 84 stores energy in a magnetic field that surrounds the inductance. When the input to the base of transistor 80 goes low, transistors 80,82 are turned off, and the collapsing magnetic field surrounding inductance 84 feeds current through diode 86 to capacitors 20,22. The energy stored on capacitors 20,22 cannot flow back through diode 86, and is isolated by power switches 26, as will be described. Thus, during alternate half-cycles of the pulsed input to convertor 16, electrical energy is incrementally stored on capacitors 20,22.

It will be noted that capacitors 20,22 of capacitor bank 18 are not referenced to electrical ground, but rather are referenced to a reference ground 90 that floats on a resistor 91 with respect to electrical ground. This un-grounded voltage across capacitor bank 18 is connected by pins J1-8 and J1-20 to voltage monitor 50 (FIGS. 1 and 3C). Voltage monitor 50 comprises a differential amplifier 50a (FIG. 3C) having inputs that receive the differential signal between the capacitor voltage and return lines, and an output connected by pins J2-14 to channel 5 of multiplexer 48 (FIGS. 1 and 2A). Thus, microprocessor 28 (FIGS. 1 and 2A) controls charging of capacitor bank 18 (FIGS. 1 and 2C) through buffer 88 and convertor 16, and at the same time monitors capacitor charge voltage through differential amplifier 50a (FIG. 3C) and multiplexer 48 (FIGS. 1 and 2A). When the charge voltage on capacitor bank 18 reaches the preselected and prestored level associated with the detector channel at which the chip has been detected, capacitor charging terminates, and microprocessor 28 generates a control signal to the appropriate channel 26a–26e (FIGS. 3A–3C) of power switches 26 (FIG. 1 and 3A–C) by setting the appropriate channel A–E of buffer 88 (FIG. 2C). Microprocessor 28 also monitors the level of supplied aircraft power through a resistive voltage divider 93 (FIG. 2C) and channel 6 of multiplexer 48 (FIG. 2A). A reference voltage is supplied to a/d multiplexer 48 by a zener diode 95.

The energy stored on the capacitor bank is, of course, related to the square of the stored voltage. About one-half second is typically required to charge capacitor bank to the twenty-eight volt level of the nominal aircraft supply voltage. If discharged directly into the chip detector as in the prior art, the discharge current can reach levels of 150 to 300 amps over a time duration of three to twenty microseconds. This high current pulse of short duration can damage the capacitors, switches, solder joints and connections, as well as cause significant radiation of electromagnetic interference in the rf range. Inductor 24, which may be on the order of sixteen microhenries, can reduce the peak current level by a factor of ten while increasing the pulse width by a factor of forty to one hundred. This reduces both electrical stress and emission of electromagnetic interference.

As shown in FIGS. 2C and 2D, power switch bank 26 contains five switch channels 26a–26e corresponding to the five chip detectors 30a–30e. Each channel 26a–26e comprises a pair of MOSFET drivers 92,94. These MOSFET drivers receive control inputs from the corresponding output channels A–E of buffer 88. Each driver 92,94 is connected to control conduction of a corresponding MOSFET power switch 96,98. The power input for each switch 96 is received on a bus 100 from inductor 24, and the power input of each MOSFET switch 98 is received from bus 102 connected to capacitor return reference 90. Thus, to apply a burn-off current to chip detector 30a, for example, drivers 92,94 of switch 26a are turned on by microprocessor 28 and channel A of buffer 88. Drivers 92,94 close respective power switches 96,98, which connect capacitor bank 18 across chip detector 30a. As noted above, capacitor bank 18 is connected to only one chip detector at a time.

Each power switch 26a–26e (FIGS. 2C–2D) has a pair of output lines (power and return) connected to associated poles of a corresponding output coupling relays 32a–32e (FIGS. 3A–3C). For example, power switches 96,98 of switch 26a are connected by pins J1-1 and J1-3 to the normally closed contacts of poles 99,101 in relay 32a. (Relays 32a–32e are illustrated in FIGS. 3A–3C in the energized condition—i.e., with power applied across the corresponding relay coils 103 under control of microprocessor 28 and channel 8 of driver 57 (FIG. 2A) through pin J1-10 (FIG. 2A and 3C).) The common contacts of poles 99,101 of relay 32a are connected by twisted-pair conductors 34a,34b to chip detector 30a (FIGS. 1 and 3A). Likewise, the outputs from the MOSFET power switches in power switch 26b (FIG. 2D) are connected by pins J1-5 and J1-7 to the normally closed contacts in double-pole relay 32b (FIG. 3B), from which the common contacts are connected to chip detector 30b. The power outputs from power switch 26c (FIG. 2D) are connected by pins J1-9 and J1-11 to relay 32c and chip detector 30c (FIG. 3B), the power outputs from power switch 26d (FIG. 2C) are connected by pins J1-13 and J1-15 to relay 32d and chip detector 30d (FIG. 3C), and the power outputs from power switch 26e (FIG. 2C) are connected by pins J1-17 and J1-18 to relay 32e and chip detector 30e (FIG. 3C). Thus, with relays 32a–32e configured as illustrated in FIGS. 3A–3C, power switches 26a–26e may be alternately activated by microprocessor 28 (FIG. 2A) and buffer 88 (FIG. 2C) for connecting both the power and return lines of capacitor bank 18 to the corresponding chip detector.

Differential amplifiers 46 (FIGS. 1 and 3A–3C) include five differential amplifiers 46a–46e having differential inputs connected to the normally closed contacts of relays 32a–32e respectively. That is, the differential inputs of each amplifier 46a–46e are connected to the discharge voltage and return outputs of the corresponding power switch 26a–26e, and thus across the corresponding chip detector 30a–30e. Each differential amplifier 46a–46e has an associated electronic switch 104a–104e connected to the differential inputs thereof. A sixth electronic switch 104f (FIG. 3C) is connected to control application of a reference zener diode 105 to the inverting inputs of amplifiers 46a–46e. Switches 104a–104f all receive a common control input through connector pin J1-19 from microprocessor 28 for configuring the differential amplifiers to monitor either for a short circuit condition at the associated chip detector indicative of detection of a chip, or a voltage condition indicative of current flow through the interconnecting cable and chip detector resistor 44 thus indicating cable and detector continuity. Microprocessor 28 thus selectively controls the input impedance and reference voltage characteristics of differential amplifiers 46a–46e for chip detection and continuity fault detection modes of operation. A continuity fault detection mode of operation may be entered by depressing switch 66 (FIGS. 1 and 2A). The outputs of differential amplifiers 46a–46e are connector by J2, pins 11,16,8,13 and 15 to channels 0–4 of a/d multiplexer 48 (FIG. 2A). Thus, microcontroller 28 selectively receives inputs from multiplexer 48 indicative of chip detection or continuity at each chip detector.

It will be noted in FIGS. 3A–3C that the normally open contact of each relay pole 101 associated with the return lines is connected to electrical ground, while the normally open contact of each pole 99 associated with the capacitor discharge lines is connected through a diode to either lamp 62 or lamp 64 (FIG. 1 and 3A). That is, the normally open contact on the discharge side of relay 32a is connected through a diode 106 to lamp 64, and the normally open contacts on the discharge sides of relays 32a–32d are each independently connected through a diode bank 108 (FIG. 3A) to lamp 62. In the event of power failure at the detection system, relays 32a–32e opened, and detectors 30a–30e are automatically connected through associated diodes 106,108 either to lamp 62 or lamp 64. Thus, for example, detection of a chip at detector 36a will function through one of the diodes 108 to illuminate lamp 62 on the pilot or operator panel, thereby warning of chip detection as in the prior art. Relays 32a–32e thus provide fail-safe operation of the chip detection system in the event of power failure at the detection circuitry.

It will thus be appreciated that the chip detection apparatus and system hereinabove described fully satisfy all of the objects and aims previously set forth. For example, provision of a microprocessor-controlled variable voltage d.c./d.c. convertor 16 provides not only the ability to program discharge voltage for each detector channel independently of the others, but also to tailor each discharge voltage to particular characteristics of the channel and/or particles expected to be detected. For example, burn-off of a two mil diameter iron test wire chip normally requires application of 28 volts at the detector contacts. However, due to losses in the interconnection cable or other operating parameters, it may be necessary in a particular system to program that channel for storage of 32 volts at capacitor bank 18. Microprocessor-controlled convertor 16 also allows operation at low input voltage since the capacitors are charged incrementally in a manner essentially independent of input voltage. As noted above, the power module outputs are fully differentiated and isolated from chassis ground. Thus, the system can be employed in conjunction with either grounded or un-grounded chip detectors.

The system and method of the present invention have been disclosed in connection with an embodiment having five chip detectors. It will be recognized, of course, that a greater number of chip detectors can be employed by adding chip detector channels, and a lesser number of chip detectors can be employed by deleting chip detection channels or leaving channels unused. In addition, chip detectors can be connected in parallel. For example, a sixth chip detector can be connected directly in parallel with chip detector 30e (FIG. 3C) across relay 32e. In the event of detection of a chip at either detector, such an event would be sensed at the control circuitry, although the control circuitry could not determine which chip detector is involved. The control circuitry would initiate a burn-off operation, which would be automatically fed to the correct detector because that detector would have a chip short circuit at the detector contacts. The input impedance of differential amplifier 46e would have to be modified to accommodate current through two chip detector resistors 44, and to distinguish when one such resistor becomes disconnected.

I claim:

1. Apparatus for monitoring particles in fluid systems comprising:

a detector for positioning in a fluid system and having electrical contacts to be bridged by particles in such system, means coupled to said detector for detecting presence of a particle bridging said contacts, first energy storage means for storing electrical energy, means for establishing a preselected level of electrical energy needed to be stored at said first energy storage means to burn off particles at said detector, and control means responsive to said detecting means for first storing said preselected level of electrical energy on said first storage means upon detection of a particle at said detector and then discharging said preselected level of energy into said detector across said contacts to burn off particles detected by said detecting means bridging said contacts.

2. The apparatus set forth in claim 1 wherein said means for storing said preselected level of electrical energy on said first energy storage means comprises means for monitoring level of energy stored on said first energy storage means, means responsive to said detecting means for charging said first energy storage means from a source of electrical power, and means responsive to said monitoring means for terminating charging of said first energy storage means when energy stored on said first energy storage means reaches said preselected level.

3. The apparatus set forth in claim 2 wherein said means for charging said first energy storage means comprises a d.c.-to-d.c. convertor for charging said first energy storage means to a preselected d.c. level from a source of d.c. electrical power.

4. The apparatus set forth in claim 3 wherein said d.c.-to-d.c. convertor comprises second energy storage means, means responsive to said control means for first storing energy in said second energy storage means from a source of d.c. power, and means for discharging said second energy storage means into said first energy storage means until energy in said first energy storage means reaches said preselected level.

5. The apparatus set forth in claim 4 wherein said control means includes means responsive to said detecting means to provide a pulsed charge control signal of alternating digital levels, means responsive to said control signal for storing electrical energy in said second energy storage means during first portions of said control signal of one digital level, and means responsive to said control signal for transferring energy from said second energy storage means to said first energy storage means during second portions of said control signal of the other digital level.

6. The apparatus set forth in claim 5 wherein said control means further comprises means responsive to said monitoring means for terminating said control signal when energy stored on such first energy storage means reaches said preselected level.

7. The apparatus set forth in claim 6 wherein said first energy storage means comprises capacitive energy storage means.

8. The apparatus set forth in claim 7 wherein said second energy storage means comprises inductive energy storage means, and wherein said means responsive to said control signal comprises switch means for establishing a current in said inductive energy storage means so as to store magnetic energy in said inductive energy storage means during said first portions of said control signal and terminating said current in said inductive energy storage means during said second portions of said control signal such that collapse of said magnetic energy in said inductive energy storage means transfers such energy as electrical energy to said capacitive energy storage means.

9. The apparatus set forth in claim 8 wherein said d.c.-to-d.c. convertor includes means for preventing reverse flow of energy from said capacitive energy storage means to said inductive energy storage means.

10. The apparatus set forth in claim 7 wherein said capacitive energy storage means includes capacitive power and return connection means.

11. The apparatus set forth in claim 10 wherein said control means further includes first and second electronic switch means respectively responsive to said control means for separately connecting said power and return connection means of said capacitive energy storage means to said contacts of said detectors.

12. The apparatus set forth in claim 11 wherein said particle detecting means comprises differential input means connected in parallel with said first and second switch means across said pair of detector contacts.

13. The apparatus set forth in claim 12 wherein said differential input means further includes means responsive to current flow through said detector for monitoring continuity of connection to said detector.

14. The apparatus set forth in claim 13 wherein said differential input means further includes means responsive to said control means for configuring said differential input means to detect particles at said detector and monitor said continuity of connection in first and second modes of operation of said differential input means.

15. The apparatus set forth in claim 14 wherein said configuring means includes means for altering input impedance characteristics of said differential input means in said first and second modes of operation.

16. The apparatus set forth in claim 7 further comprising inductive means connected between said capacitive energy storage means and said detector for increasing time duration of discharge of said capacitance energy storage means through said detector.

17. The apparatus set forth in claim 7 comprising a plurality of said detectors, wherein said detecting means comprises means for detecting presence of a particle bridging the contacts at any of said detectors, and wherein said control means comprises means for discharging said first energy storage means into a detector at which a particle is detected.

18. The apparatus set forth in claim 17 wherein said control means further comprises means for storing a said preselected energy level for each of said detectors, and means for storing electrical energy at said first energy storage means upon detection of a particle at one of said detectors to the preselected level associated with such detector.

19. Apparatus for monitoring particles in fluid systems comprising:
   a particle detector for positioning in a fluid system and having electrical contacts to be bridged by particles in such system, and
   a microprocessor-based control system that includes:
   capacitive energy storage means,
   means coupled to said detector for detecting presence of a particle bridging said contacts,
   means for storing information indicative of level of electrical energy needed to be stored at said capacitive energy storage means to burn off particles at said detector,
   means for monitoring energy stored on said capacitive storage means,
   charging means responsive to said detecting means, said monitoring means and said storing means for storing electrical energy at said capacitive energy storage means at said level upon detection of a particle at said detector, and
   means for discharging said capacitive energy storage means through said detector.

20. The apparatus set forth in claim 19 wherein said charging means comprises means for pulsed storage of electrical energy on said capacitive energy storage means, means responsive to said monitoring means for comparing energy on said capacitive storage means to said level, and means for terminating said pulsed storage of energy on said capacitive energy storage means when stored energy on said capacitive energy storage means reaches said level.

21. The apparatus set forth in claim 20 wherein said means for pulsed storage of electrical energy on said capacitive discharge storage means comprises means for generating a pulsed charge control signal of alternating digital polarities, second energy storage means, and electronic switch means responsive to said pulsed charge control signal for storing energy in said second storage means during portions of said control signal of one polarity and transferring such electrical energy to said capacitive energy storage means during portions of said control signal of the other polarity.

22. The apparatus set forth in claim 21 wherein said second energy storage means comprises inductive energy storage means, and wherein said switch means draws electrical current through said inductive energy storage means and thereby stores magnetic energy in said inductive energy storage means during said first portions of said control signal and transfers such magnetic energy as electrical energy to said capacitive energy storage means during said second portions of said control signal.

23. The apparatus set forth in claim 19 wherein said means for discharging said capacitive energy storage means through said detector comprises an inductor connected between said capacitive energy storage means and said detector for reducing rate of discharge of energy through said detector.

24. The apparatus set forth in claim 19 wherein said capacitive energy storage means has voltage and return lines isolated from electrical ground, and wherein said discharging means comprises switch means for independently applying said voltage and return lines to said detector contacts.

25. The apparatus set forth in claim 24 wherein said detecting means comprises differential input means connected to said detector contacts in parallel with said switch means.

26. The apparatus set forth in claim 25 wherein said differential input further includes means responsive to current flow through said detector for monitoring continuity of connection to said detector.

27. The apparatus set forth in claim 26 wherein said differential input means further includes means responsive to said control system for configuring said differential input means to detect particles at said detector and monitor said continuity of connection in first and second mode of operation of said differential input means.

28. The apparatus set forth in claim 27 wherein said configuring means includes means for altering input impedance characteristics of said differential input means in said first and second modes of operation.

29. The apparatus set forth in claim 19 further comprising means responsive to said detecting means for indicating detection of a particle at said detector.

30. The apparatus set forth in claim 29 further comprising fail-safe means connected between said control system and said detector for normally connecting said control system to said detector and being responsive to failure at said control system for connecting said detector directly to said indicating means.

31. The apparatus set forth in claim 19 wherein said detector comprises a plurality of said detectors, wherein said detecting means comprises means for detecting presence of a particle bridging the contacts at any of said detectors, and wherein said control system further comprises means for discharging said capacitive energy storage means into any of said detectors at which a particle is detected.

32. The apparatus set forth in claim 31 wherein said control system further comprises means for storing information indicative of a preselected energy level for each of said detectors, and means for storing electrical energy at said capacitive energy storage means upon detection of a particle at one of said detectors to the preselected level associated with such detector.

33. The apparatus set forth in claim 19 further comprising an input/output port connected to said control system for operating said control system independently of said detector and detection of particles at said detector.

34. The apparatus set forth in claim 33 wherein said control system further includes non-volatile memory means, means for storing information in said non-volatile memory means indicative of operation of said apparatus, and means for selectively reading said non-volatile memory means through said input/output port.

35. Apparatus for monitoring particles in a fluid systems comprising:
   a plurality of particle detectors for positioning in one or more fluid systems, each of said detectors including detector contacts that are bridged by particles in the associated systems, and
   microprocessor-based control means that includes:
   capacitive energy storage means,
   means coupled to each of said detectors for detecting presence of a particle bridging the contacts of the associated detector,
   means for storing information independently for each said detector indicative of a level of electrical energy needed at each said detector to burn off particles at the detector, means responsive to said detecting means for identifying the detector at which a particle is detected, means responsive to said identifying means and said storing means for charging said capacitive energy storage means upon detection of a particle to an energy level in said storing means for the detector identified by said identifying means, and means for discharging the electrical energy on said capacitive energy storage means through the detector identified by said identifying means.

36. Apparatus for monitoring particles in fluid systems comprising:

a particle detector for positioning in a fluid system and having electrical contacts to be bridged by particles in such system, and control means for monitoring said detector, detecting particles at said detector and burning off particles at said detector, said control means comprising:

capacitive energy storage means having energy discharge and return output means isolated within said control means from electrical ground, means for storing a predetermined level of electrical energy on said capacitive energy storage means, means for detecting a particle bridging said contacts at said detector, and electronic switch means responsive to said detecting means for separately and simultaneously connecting said energy discharge and return output means to respective contacts of said detector.

37. The apparatus set forth in claim 36 further comprising an inductor connected between said energy discharge output means and said switch means.

38. The apparatus set forth in claim 36 wherein said detecting means comprises differential input means connected to said detector contacts in parallel with said switch means.

39. The apparatus set forth in claim 38 wherein said differential input means further includes means responsive to current flow through said detector for monitoring continuity of connection to said detector.

40. The apparatus set forth in claim 39 wherein said differential input means further includes means responsive to said control means for configuring said differential input means to detect particles at said detector and monitor said continuity of connection in first and second mode of operation of said differential input means.

41. The apparatus set forth in claim 40 wherein said configuring means includes means for altering input impedance characteristics of said differential input means in said first and second modes of operation.

42. The apparatus set forth in claim 36 further comprising means responsive to said detecting means for indicating detection of a particle at said detector.

43. The apparatus set forth in claim 42 further comprising fail-safe means connected between said control means and said detector for normally connecting said control means to said detector and being responsive to failure at said control means for connecting said detector directly to said indicating means.

44. Apparatus for monitoring particles in fluid systems comprising:

a detector for positioning in a fluid system and having electrical contacts for bridging by particles in the system, means coupled to said detector from detecting presence of a particle bridging said contacts, capacitive energy storage means for storing electrical energy at a predetermined level, and means responsive to said detecting means for discharging said capacitive energy storage means through said detector to burn off the particle detected by said detecting means, including inductance means connected between said capacitive energy storage means and said detector to control waveform shape of energy applied to said detector and reduce radiation of electromagnetic interference from said apparatus.

45. The apparatus set forth in claim 44 comprising a plurality of said detectors, and switch means responsive to said detecting means for selectively connecting said capacitive energy storage means and said inductance means to a one of said detectors at which a particle has been detected.

46. A method of burning off particulate debris in a fluid debris monitoring system having a plurality of particle detectors disposed in fluid, said method comprising the steps of:

(a) indentifying a detector from among said plurality of detectors at which particulate debris has been detected, (b) storing electrical energy on a charge storage capacitor at a level correlated with the specific detector identified in said step (a), and (c) discharging said electrical energy stored in said step (b) through the detector identified in said step (a).

47. The method set forth in claim 46 comprising the additional steps of:

(d) identifying another detector at which particulate debris has been detected, (e) storing electrical energy on the same said storage capacitor at a level correlated with the specific detector identified in said step (d), and (f) discharging said electrical energy stored in said step (e) through the detector identified in step (d).

48. The method set forth in claim 47 wherein said energy level stored in said step (e) is different from said energy level stored in said step (b).

49. The method set forth in claim 46 wherein said step (c) is carried out by discharging said energy through an inductor into said detector.

50. The method set forth in claim 46 wherein said step (b) is carried out by (b1) pumping energy onto said capacitor in incremental stages.

51. The method set forth in claim 50 wherein said step (b) includes the further steps of: (b2) monitoring energy level on said capacitor, and (b3) terminating said step (b1) when said energy level reaches said level correlated with said specific detector.

52. The method set forth in claim 50 wherein said step (b1) is carried out by: (b1a) storing a predetermined amount of energy in an inductor, (b1b) transferring said energy stored in said step (b1a) onto said capacitor, and (b1c) repeating said steps (b1a) and (b1b) in sequence.

* * * * *